United States Patent [19]

Faul et al.

[11] Patent Number: 5,726,266
[45] Date of Patent: Mar. 10, 1998

[54] COPOLYMERS BASED ON DIKETENES, ETHYLENICALLY UNSATURATED DICARBOXYLIC ACIDS OR DICARBOXYLIC ACID DERIVATIVES AND ETHYLENICALLY UNSATURATED HYDROCARBONS

[75] Inventors: Dieter Faul, Niederkirchen; Joachim Roser, Mannheim; Heinrich Hartmann, Limburgerhof; Gabriele Dralle-Voss, Darmstadt; Knut Oppenländer, Ludwigshafen; Bernd Wenderoth, Birkenau, all of Germany

[73] Assignee: BASF Aktiengesellschaft, Ludwigshafen, Germany

[21] Appl. No.: 704,751

[22] PCT Filed: Mar. 11, 1995

[86] PCT No.: PCT/EP95/00904

§ 371 Date: Sep. 24, 1996

§ 102(e) Date: Sep. 24, 1996

[87] PCT Pub. No.: WO95/25755

PCT Pub. Date: Sep. 28, 1995

[30] Foreign Application Priority Data

Mar. 24, 1994 [DE] Germany .......................... 44 10 198.8

[51] Int. Cl.[6] .................. C08F 224/00; C08F 222/02; C08F 222/10; C08F 210/00
[52] U.S. Cl. ................. 526/266; 526/316; 526/318.2; 526/321; 526/348
[58] Field of Search ................... 526/316, 266, 526/318.2, 321, 348

[56] References Cited

U.S. PATENT DOCUMENTS

| | | |
|---|---|---|
| 3,048,479 | 8/1962 | Ilnyckyj et al. . |
| 3,627,838 | 12/1971 | Ilnyckyj et al. . |
| 4,009,110 | 2/1977 | Tofl et al. ...................... 526/316 |
| 5,016,863 | 5/1991 | Birkmair . |
| 5,576,396 | 11/1996 | Wang et al. ...................... 525/367 |

FOREIGN PATENT DOCUMENTS

| | | |
|---|---|---|
| 2 342 300 | 4/1974 | Germany . |
| 25 31 194 | 2/1976 | Germany . |
| 39 13 112 C2 | 5/1992 | Germany . |

*Primary Examiner*—Joseph L. Schofer
*Assistant Examiner*—Wu C. Cheng
*Attorney, Agent, or Firm*—Oblon, Spivak, McClelland, Maier & Neustadt, P.C.

[57] ABSTRACT

Copolymers comprise a) from 1 to 65 mol % of at least one diketene of the general formula I

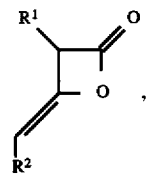

where $R^1$ and $R^2$, independently of one another, are each hydrogen or $C_1$–$C_{30}$-alkyl, b) from 30 to 70 mol % of at least one ethylenically unsaturated dicarboxylic acid or one dicarboxylic acid derivative, c) from 0.5 to 60 mol % of at least one ethylenically unsaturated hydrocarbon and d) up to 20 mol % of at least one further ethylenically unsaturated monomer, modified copolymers are obtainable by reacting these copolymers with NH-, SH- and/or OH-functional compounds, and the unmodified or modified copolymers are used as additives for mineral oil middle distillates.

9 Claims, No Drawings

COPOLYMERS BASED ON DIKETENES, ETHYLENICALLY UNSATURATED DICARBOXYLIC ACIDS OR DICARBOXYLIC ACID DERIVATIVES AND ETHYLENICALLY UNSATURATED HYDROCARBONS

BACKGROUND OF THE INVENTION

1. Field of the Invention

The present invention relates to copolymers based on diketenes, ethylenically unsaturated dicarboxylic acids or dicarboxylic acid derivatives and ethylenically unsaturated hydrocarbons, a process for their preparation, modified copolymers obtainable by reaction with NH-, SH- and/or OH-functional compounds, the use of the unmodified or modified copolymers as additives for mineral oil middle distillates, and mineral oil middle distillates containing said copolymers.

2. Discussion of the Background

Middle distillates, such as gas oils, diesel oils or heating oils, which are obtained by distillation of mineral oils, have different paraffin contents, depending on the origin of the crude oil. At lower temperatures, solid paraffins separate out (cloud point, CP). On further cooling, the lamellar n-paraffin crystals form a house-of-cards structure and the middle distillate sets although the predominant part of the middle distillate is still liquid. The flow of the power fuels obtained from mineral oil distillates is considerably adversely affected by the precipitated n-paraffins in the temperature range between cloud point and pour point. The paraffins block filters and cause irregular feed of the power fuel to the combustion units or completely stop said feed. Similar problems occur in the case of heating oils.

It has long been known that the crystal growth of the paraffins in the combustion fuels and power fuels obtained from mineral oil middle distillates can be modified by suitable additives. Effective additives prevent middle distillates from forming such house-of-cards structures and becoming solid at a few degrees centigrade below the temperature at which the first paraffin crystals form. Instead, fine, well crystallized, separate paraffin crystals are formed, which pass through filters in motor vehicles and heating systems or at least form a filtercake which is permeable to the liquid part of the middle distillates, so that trouble-free operation is ensured.

Ethylene/vinyl carboxylate copolymers, as disclosed in, for example, U.S. Pat. No. 3,048,479 and U.S. Pat. No. 3,627,838, have long been used as flow improvers.

A disadvantage of these additives is that the precipitated paraffin crystals have a higher density than the liquid part and therefore tend increasingly to separate out on the bottom of the container during storage. Consequently, a homogeneous phase having a low paraffin content forms in the upper part of the container and a two-phase paraffin-rich layer at the bottom. Since both in vehicle tanks and in storage or delivery tanks of mineral oil dealers the middle distillate is generally taken off slightly above the bottom of the container, there is a danger that the high concentration of solid paraffins will lead to blockages of filters and metering means. This danger is all the greater the further the storage temperature falls below the precipitation temperature of the paraffins, since the precipitated amount of paraffin increases with decreasing temperature.

The paraffin crystal modifiers, ie. flow improvers or paraffin dispersants, are in general polymers which change the crystal growth of the n-paraffins by cocrystallization (interaction) and improve the flow properties of the middle distillate at low temperatures. According to DIN EN 116, the efficiency of the flow improvers is expressed indirectly by measurement of the cold filter plugging point (CFPP).

DE-A-2 342 300 discloses copolymers of maleic anhydride (MA) and diketene. These copolymers or the completely or partially hydrolyzed form thereof are described as being suitable products for the preparation of surfactant compounds, hairspray compositions, glass cleaners, textile assistants or binders for strengthening nonwovens and paper.

DE-A-2 531 194 and DE-A-2 531 195 describe MA/diketene copolymers and MA/diketene/vinyl ether copolymers and reaction products thereof with alcohols of 1 to 18 carbon atoms, polyethylene glycol monoalkyl ethers and mixtures of the two. These are used in particular in textile assistants and hair cosmetics.

DE-A-3 913 127 describes copolymers based on MA/diketene and acrylic acid. After they have been isolated or, if required, after solvolysis, these polymers are suitable as detergent additives.

SUMMARY OF THE INVENTION

It is an object of the present invention to provide copolymers which ensure the flow of mineral oil distillates at low temperature by having a dispersing effect so that settling out of precipitated paraffins is delayed or prevented. The flow improvers should display their activity regardless of the composition of the mineral oil middle distillates.

We have found that this object is achieved by copolymers of a) from 1 to 65 mol % of at least one diketene of general formula I

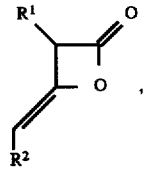

where $R^1$ and $R^2$, independently of one another, are each hydrogen or $C_1$–$C_{30}$-alkyl, b) from 30 to 70 mol % of at least one ethylenically unsaturated dicarboxylic acid or one dicarboxylic acid derivative, c) from 0.5 to 60 mol % of at least one ethylenically unsaturated hydrocarbon and d) up to 20 mol % of at least one further ethylenically unsaturated monomer.

The present invention further relates to modified copolymers which are suitable as paraffin dispersants and are obtainable by reacting the abovementioned copolymers with NH-, SH- and/or OH-functional compounds, the use of the unmodified or modified copolymers as additives for mineral oil middle distillates, and mineral oil middle distillates containing these copolymers.

The present invention also relates to a process for the preparation of copolymers, wherein a) from 1 to 65 mol % of at least one diketene of the general formula I

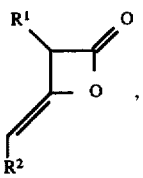

where $R^1$ and $R^2$, independently of one another, are each hydrogen or $C_1$-$C_{30}$-alkyl,
b) from 30 to 70 mol % of at least one ethylenically unsaturated dicarboxylic acid or one dicarboxylic acid derivative,
c) from 0.5 to 60 mol % of at least one ethylenically unsaturated hydrocarbon and
d) up to 20 mol % of at least one further ethylenically unsaturated monomer are reacted in the presence of a free radical polymerization initiator.

DETAILED DESCRIPTION OF THE PREFERRED EMBODIMENTS

The novel copolymers contain, as an essential polymerized component, from 1 to 65, preferably from 10 to 50, mol % of at least one diketene of the general formula I (component a)).

An example of a substituted diketene is the distearyldiketene in which $R^1$ and $R^2$ are each of 14 to 16 carbon atoms, which is sold under the name Basoplast® by BASF Aktiengesellschaft. According to the invention, the unsubstituted diketene (where $R^1$ and $R^2$ are each hydrogen) is preferably used.

The novel copolymers contain from 30 to 70, preferably from 40 to 60, mol % of at least-one ethylenically unsaturated dicarboxylic acid or one dicarboxylic acid derivative (component b)) as polymerized units.

Examples of suitable components b) are monoethylenically unsaturated dicarboxylic anhydrides of 4 to 8 carbon atoms, eg. maleic anhydride, itaconic anhydride, mesaconic anhydride, citraconic anhydride and methylenemalonic anhydride. Among the stated anhydrides, maleic anhydride and itaconic anhydride are preferably used, maleic anhydride being very particularly preferred.

For example, fumaric acid, maleic acid, itaconic acid, mesaconic acid, citraconic acid, methylenemalonic acid and esters thereof are also suitable.

The ethylenically unsaturated dicarboxylic acids or dicarboxylic acid derivatives which are preferred according to the invention may be summarized by the general formula II

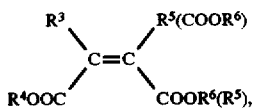

where $R^3$ to $R^6$, independently of one another, are each hydrogen or a $C_1$-$C_{22}$-alkyl radical which may contain hetero atoms, and, in the case of cis-dicarboxylic acids of the formula II (where $R^4$ and $R^6$ are each H), the anhydrides thereof may also be used.

The novel copolymers contain, as a further essential component, from 0.5 to 60, preferably from 5 to 40, mol % of at least one ethylenically unsaturated hydrocarbon (component c)). Preferably used components c) are ethylenically unsaturated hydrocarbons of the general formula III

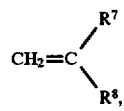

where $R^7$ is hydrogen or $C_1$-$C_{10}$-alkyl and $R^8$ is alkyl, alkenyl or aryl. Suitable compounds c) are, for example, α-olefins, such as 1-butene, 1-hexene, 1-octene, 1-decene, 1-dodecene, 1-tetradecene, 1-hexadecene, 1-octadecene or mixtures of 1-alkenes of 20 to 24 carbon atoms or of 24 to 28 carbon atoms or longer-chain polyethylene derivatives having a terminal C-C double bond. Polymeric propene, butene and isobutene derivatives which have an unsaturated terminal group are also useful. Aryl-substituted olefins, eg. styrshe, are also suitable.

The novel copolymers may furthermore contain up to 20 mol % of at least one further ethylenically unsaturated monomer (component d)). Examples of monomers d) are acrylic acid, methacrylic acid, esters derived therefrom and vinyl ethers and vinyl esters.

The polymerization of components a), b), c) and, if required, d) is carried out in general in a manner known per se, in an inert organic solvent under free radical conditions (cf. DE-A-23 42 300 and DE-A-25 31 135). Solvents which virtually do not participate at all in the polymerization and do not react with the monomers are particularly suitable. Such solvents, which may be used alone or as a mixture, are, for example, acetone, methyl ethyl ketone, diethyl ketone, cyclohexanone, tetrahydrofuran, dioxane, ethyl acetate, ethyl propionate, aromatic hydrocarbons, such as benzene, toluene, xylene, cumene, tetralin or solvent naphtha (eg. Solvesso® 150), aliphatic hydrocarbons, such as pentane, hexane, heptane, octane, isooctane, cyclohexane, decalin or Shellsol® D70, and aliphatic halohydrocarbons, such as dichloromethane, dichloroethane or trichloroethane.

Solvesso® 150 is EXXON Chemical GmbH's name for an aromatic solvent fraction having a boiling range from 187° to 203° C. It contains about 99% of aromatics. Shellsol® D70 is Shell's name for a dearomatized, aliphatic hydrocarbon mixture having a boiling range of from 195° to 245° C.

Acetone, methyl ethyl ketone, toluene, xylene, tetralin, decalin, solvent naphtha (eg. Solvesso® 150) or Shellsol® D70 is preferably used as the solvent.

The copolymerization of components a), b), c) and, if required, d) is carried out, as a rule, in the presence of compounds which decompose into free radicals under the polymerization conditions. Examples of suitable polymerization initiators are hydrogen peroxide, organic peroxides and hydroperoxides, azo compounds and peroxodisulfates. The polymerization can also be carried out by the action of high-energy radiation or by irradiation of the reaction mixture in the presence of a photoinitiator, for example benzoin.

The initiators should preferably have a half-life of <3 hours at the chosen polymerization temperatures. Preferably used polymerization initiators are tert-butyl perpivalate, dilauryl peroxide, tert-butyl per-2-ethylhexanoate (tert-butyl peroctoate), tert-butyl perbenzoate, dicumyl peroxide, di-tert-butyl peroxide and 2,2'-azobis(2-methylpropionitrile), alone or as a mixture. The half-lives of the stated peroxides can be reduced by the presence of redox coinitiators, for example benzoin or dimethylaniline, and of complexes or salts of heavy metals, such as copper, cobalt, manganese, iron, nickel or chromium, which are soluble in organic solvents.

The polymerization initiators which decompose into free radicals are used in conventional amounts, for example from 0.1 to 5.0% by weight, based on the amounts of monomers used in the polymerization.

The copolymerization may be carried out in the presence or absence of conventional regulators, such as mercaptoethanol, mercaptopropanol, mercaptoacetic acid, mercaptopropionic acid, thiolactic acid, n-butyl mercaptan, tert-butyl mercaptan, octyl mercaptan or dodecyl mercaptan. Further suitable regulators are aldehydes, such as acetaldehyde, propionaldehyde or butyraldehyde, and formic acid.

The polymerization is preferably carried out in stirred kettles which are equipped, for example, with an anchor stirrer, paddle stirrer or impeller stirrer. The copolymerization can be effected, for example, as a solution, precipitation or suspension polymerization. In the precipitation and suspension polymerization, it may be advantageous to carry out polymerization additionally in the presence of protective colloids. Examples of suitable protective colloids are copolymers of maleic anhydride and vinyl alkyl ethers which contain 1 to 20 carbon atoms in the alkyl group, or copolymers of maleic anhydride and olefins of 8 to 20 carbon atoms and monoesters thereof with $C_{10}$–$C_{20}$-alcohols or monoamides with $C_{10}$–$C_{20}$-amines. Polyalkyl vinyl ethers whose alkyl group is of 1 to 20 carbon atoms, for example polymethyl, polyethyl and polyisobutyl vinyl ether, are also useful. If a protective colloid is used in the copolymerization, the effective amounts are from 0.05 to 4.0% by weight, based on the monomers a), b), c) and, if required, d) to be polymerized.

The concentration of the monomers in the inert organic solvents is in general from 5 to 80, preferably from 15 to 60, % by weight. The polymerization temperature is as a rule from 40° to 160° C., preferably from 50° to 150° C.

After the end of the polymerization, the copolymers can be isolated, for example by distilling off the solvent used in the polymerization or by precipitating the polymers using a suitable solvent. The copolymers then remain as a pulverulent residue.

The weight average molecular weight of the novel copolymers is in general from 300 to 50 000, preferably from 500 to 10 000.

The copolymers can be used as such in mineral oil middle distillates. However, they are preferably modified by polymer-analogous reactions.

The novel copolymers contain, as reactive groups, in particular carboxyl, anhydride and ester structural units and structural units comprising a lactone having a 4-membered ring. In addition to simple hydrolysis with water, reactions with NH-, SH- and OH-functional compounds are also advantageous.

Examples of suitable reactants are alcohols, phenols, mercaptans, oximes, imines and primary and secondary amines. The reaction of the copolymers can be carried out here in the organic solvent in which the copolymerization was also carried out, or the solvents used are first distilled off and the corresponding reactions are then carried out.

The alcohols used may be in particular branched or straight-chain $C_1$–$C_{30}$-alkyl alcohols or alkenyl alcohols, preferably $C_{12}$–$C_{30}$-alkyl or alkenyl alcohols, for example isotridecanol, stearyl alcohol, tallow fatty alcohol or behenyl alcohol. Alkoxylates of alcohols, amines, amides or carboxylic acids may also be used, for example alkoxylation products of distearylamine, oleylamine, di-tallow fatty amine, hydrogenated di-tallow fatty amine, di-coconut fatty amine, aminopropylstearylamine, stearyl alcohol, isotridecanol, isotridecylamine or behenyl alcohol.

The amines used may be primary or secondary alkylamines, polyetheramines or polyamines.

Examples of primary or secondary amines are isotridecylamine, stearylamine, coconut fatty amine, distearylamine, di-tallow fatty amine, dioleylamine and di-coconut fatty amine. Polyamines may also be used, for example aminopropylstearylamine, aminopropyllaurylamine, N,N-dimethylpropylenediamine or N,N-dimethyldipropylenetriamine. Aminopropylated alcohols, aminated alkoxylates or aminopropylated alkoxylates may also be used as amine components, for example aminopropylstearyl alcohol, aminopropylethoxystearylamine or fatty alkyl-polyethylene glycol-amine (aminated Lutensol® brands from BASF Aktiengesellschaft).

Particularly suitable modified copolymers are obtainable by reacting the novel copolymers with NH- and/or OH-functional compounds of the general formula IV

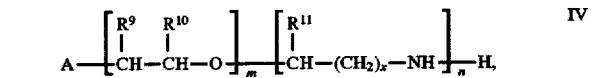

where
m may be from 0 to 100, n from 0 to 5 and x from 0 to 5, $R^9$, $R^{10}$ and $R^{11}$, independently of one another, are each hydrogen or $C_1$–$C_5$-alkyl and
A is $NR^{12}R^{13}$ or $C_2$–$C_{30}$-alkoxy,
and at least one of the substituents $R^{12}$ or $R^{13}$ is not hydrogen and is $C_1$–$C_{30}$-alkyl or alkenyl or a polyether radical

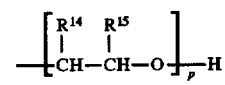

where $R^{14}$ and $R^{15}$, independently of one another, are each hydrogen or $C_1$–$C_5$-alkyl and p is from 1 to 100.

The $C_1$–$C_{30}$-alkyl or alkenyl radical forming $R^{12}$ and/or $R^{13}$ is preferably $C_3$–$C_{30}$-alkyl, particularly preferably $C_{14}$–$C_{24}$-alkyl, which may be polyunsaturated and straight-chain or branched.

In a preferred embodiment of the modified copolymers, m or n is 0.

Examples of compounds of the formula IV where m is 0 are distearylamine, di-tallow fatty amine, dioleylamine, di-coconut fatty amine, aminopropylstearylamine and aminopropyllaurylamine.

Examples of further compounds of the formula IV where n is 0 and A is $NR^{12}R^{13}$ are the alkoxylation products of distearylamine, oleylamine, di-tallow fatty amine, hydrogenated tallow fatty amine, di-coconut fatty amine or aminopropylstearylamine. When n is 0, m is preferably from 1 to 10. Alkoxylated stearylamine and alkoxylated distearylamine, eg. hydroxyethyldistearylamine, are particularly preferred.

The reaction of the novel copolymers with alcohols and amines or derivatives thereof is carried out in the absence of a solvent or in solvents which themselves generally contain no acidic hydrogen atoms. The solvents used may be the same as those employed in the polymerization. The reaction need not go to completion. The amido and ester groups formed during the reaction and the decrease in the concentration of the lactone having a 4-membered ring can be monitored by IR spectroscopy. At the same time, a decrease in the acid number [mg KOH/g] is observed.

The alcohol or amine component is usually used in amounts of from 0.1 to 3 gram equivalents per gram equivalent of polymerized dicarboxylic acid (derivative), based on the OH or NH gram equivalents of said alcohol or amine component. Amounts of from 0.5 to 2 gram equivalents of NH or OH per dicarboxylic acid (derivative) unit are preferred.

The reaction products of the novel copolymers with fatty alcohols, such as stearyl alcohol, tallow fatty alcohol or behenyl alcohol, or alkoxylated fatty alcohols (eg. Lutensol® AT brands from BASF AG) and with primary and secondary alkylamines have proven particularly suitable paraffin dispersants for middle distillates.

The novel unmodified or modified copolymers are used as additives for mineral oil middle distillates, which are understood as meaning petroleum, heating oil and diesel fuels having a boiling point of from about 150° to 400° C. The copolymers may be added to the middle distillates directly but are preferably added in the form of a 20-70% strength by weight solution. Suitable solvents are aliphatic or aromatic solvents, such as xylene or mixtures thereof, as well as high-boiling mixtures of aromatics, and middle distillates. The amount of copolymers in the mineral oil middle distillates is as a rule from 10 to 10 000, preferably from 20 to 5000, particularly preferably from 50 to 1000, ppm. Depending on the intended use, the middle distillates may also contain further additives, such as flow improvers, dispersers, antifoams, corrosion inhibitors, antioxidants, demulsifiers, lubricity improvers, conductivity improvers and/or dyes.

Such middle distillates usually already contain conventional flow improvers which are described in detail in the patent literature, for example in DE-A-19 14 756 and EP-A-486 836 (ethylene/vinyl ester copolymers and mixtures thereof with other copolymers), EP-A-214 876 ($\alpha$-olefin/maleic anhydride copolymers) or EP-A-155 807 (alkyl fumarate/vinyl acetate copolymers).

However, copolymers which contain further comonomers in addition to ethylene and vinyl esters or acrylates are also suitable. The molecular weight of these flow improvers is, as a rule, from 500 to 5000, preferably from 1000 to 3000.

The novel copolymers result in a substantial improvement in the low-temperature flow properties of the middle distillates, regardless of their origin, by keeping the precipitated paraffin crystals effectively in suspension so that there are no blockages of filters or pipes by paraffin which has settled out. They have a broad activity and thus ensure that the precipitated paraffin crystals in various middle distillates are very well dispersed.

EXAMPLES

In the examples which follow, percentages are by weight. The K values were determined according to H. Fikentscher, Cellulose-chemie 13 (1932), 58–64 and 71–74.

A) Preparation of the copolymers

A glass reactor which was provided with a stirrer and three feeds was used for the preparation of the copolymers, and the procedure was carried out under nitrogen. One feed was heatable and was brought to 65° C. for the solution of maleic anhydride in Solvesso® 150. The IR spectrum of the copolymers each showed characteristic bands at 1840 cm$^{-1}$ (lactone, anhydride) and 1780 cm$^{-1}$ (anhydride).

A1)

27.9 g of an $\alpha$-olefin from the $C_{20}$–$C_{24}$ fraction (Gulftene® 20–24, trademark of Chevron) and 52 g of Solvesso® 150 were initially taken in the reactor and heated to 90° C. Thereafter, 45.6 g of maleic anhydride, dissolved in 40 g of Solvesso® 150, and 34 g of diketene were added in the course of 3 hours. At the same time, a solution of 2.72 g of tert-butyl peroctoate in 40 g of Solvesso® 150 was added in the course of 3.5 hours. After the end of the initiator addition, the reaction mixture was stirred for a further 2 hours at 100° C. A yellow, viscous solution having a solids content of 28.3% was obtained. After the solution had been evaporated down under reduced pressure, the polymer was obtained as a yellow powder having a K value of 22.5 (2% strength in xylene).

A2)

97.8 g of an $\alpha$-olefin from the $C_{20}$–$C_{24}$ fraction (Gulftene® 20–24) and 32 g of Solvesso® 150 were initially taken and heated to 90° C. Thereafter, 40.8 g of maleic anhydride, dissolved in 35 g of Solvesso® 150, and 7.8 g of diketene, dissolved in 35 g of Solvesso® 150, were added in the course of 3 hours. At the same time, a solution of 3.6 g of tert-butyl peroctoate in 38 g of Solvesso® 150 was added in the course of 3.5 hours. After the end of the initiator addition, the reaction mixture was stirred for a further 2 hours at 100° C. A yellow, viscous solution having a solids content of 47.7% was obtained. After the solution had been evaporated down under reduced pressure, the polymer was obtained as a yellow powder having a K value of 12.5 (5% strength in xylene).

A3)

37.3 g of an $\alpha$-olefin from the $C_{24}$–$C_{28}$ fraction (Gulftene® 24–28) and 50 g of Solvesso® 150 were initially taken in the reactor and heated to 90° C. Thereafter, 50.2 g of maleic anhydride, dissolved in 35 g of Solvesso® 150, and 37.7 g of diketene were added in the course of 3 hours. At the same time, a solution of 3.14 g of tert-butyl peroctoate in 40 g of Solvesso® 150 was added in the course of 3.5 hours. After the end of the initiator addition, the reaction mixture was stirred for a further 2 hours at 100° C. A yellow, viscous solution having a solids content of 27.3% was obtained. After the solution had been evaporated down under reduced pressure, the polymer was obtained as a yellow powder having a K value of 17.5 (2% strength in xylene).

A4)

145.8 g of an $\alpha$-olefin from the $C_{24}$–$C_{28}$ fraction (Gulftene® 24–28) and 50 g of Solvesso® 150 were initially taken in the reactor and heated to 90° C. Thereafter, 49 g of maleic anhydride, dissolved in 30 g of Solvesso® 150, and 9.4 g of diketene, dissolved in 35 g of Solvesso® 150, were added in the course of 3 hours. At the same time, a solution of 3.6 g of tert-butyl peroctoate in 55 g of Solvesso® 150 was added in the course of 3.5 hours. After the end of the initiator addition, the reaction mixture was stirred for a further 2 hours at 100° C. A yellow, viscous solution having a solids content of 52.6% was obtained. After the solution had been evaporated down under reduced pressure, the polymer was obtained as a yellow powder having a K value of 13.5 (5% strength in xylene).

A5)

78.0 g of an $\alpha$-olefin based on polyisobutene having a weight average molecular weight of 1000 (PIB [1000], Glissopal® ES 3250 from BASF Aktiengesellschaft) and 52 g of Solvesso® 150 were initially taken in the reactor and the solution was heated to 90° C. Thereafter, 38.2 g of maleic anhydride, dissolved in 35 g of Solvesso® 150, and 29.0 g of diketene were added in the course of 3 hours. Together with the addition of monomers, a solution of 3.6 g of tert-butyl peroctoate in 55 g of Solvesso® 150 was metered in over 3.5 hours. After the end of the initiator addition, the reaction mixture was stirred for a further 2 hours at 100° C. A yellow, viscous solution having a solids content of 43.3% was obtained. After the solution had been evaporated down under reduced pressure, the polymer could be isolated in the form of a yellow powder. The polymer had a K value of 18.5 (5% strength in xylene).

A7)

30.4 g of maleic anhydride and 65 g of Solvesso® 150 were initially taken in the reactor and heated to 90° C. Thereafter, 6.5 g of styrene, dissolved in 25 g of Solvesso® 150, and 23 g of diketene, dissolved in 25 g of Solvesso® 150, were added in the course of 3 hours. Together with the addition of monomers, a solution of 1.5 g of tert-butyl peroctoate in 25 g of Solvesso® 150 was metered in over 3.5 hours. After the end of the initiator addition, the reaction mixture was stirred for a further 2 hours at 100° C. A yellow, oily suspension having a solids content of 26.7% was obtained. After filtration under suction and drying, the polymer was obtained in the form of a slightly yellow powder.

A8)

29.4 g of maleic anhydride and 60 g of Solvesso® 150 were initially taken in the reactor and heated to 90° C.

Thereafter, 25 g of styrene, dissolved in 25 g of Solvesso® 150, and 5.6 g of diketene, dissolved in 25 g of Solvesso® 150, were added in the course of 3 hours. Together with the addition of monomers, a solution of 1.5 g of tert-butyl peroctoate in 25 g of Solvesso® 150 was metered in over 3.5 hours. After the end of the initiator addition, the reaction mixture was stirred for a further 2 hours at 100° C. A yellow, oily suspension having a solids content of 31.8% was obtained. After filtration under suction and drying, the polymer was obtained in the form of a slightly yellow powder.

A9)

A solution of 70.9 g of distearyldiketene, 16.3 g of MA and 9.9 g of an α-olefin from the $C_{24}$–$C_{28}$ fraction (Gulftene® 20–24) in 24 g of Solvesso® 150 was initially taken in the reactor and heated to 90° C. A solution of 4.85 g of butyl peroctoate in 25 g of Solvesso® 150 was added in the course of 3.5 hours. After the end of the feed, polymerization was continued for a further 2 hours at 95° C.

The viscous solution thus obtained had a solids content of 66.9% and was reacted directly without further working up.

A10)

A solution of 78.8 g of distearyldiketene, 18.15 g of MA and 2.5 g of Lutonal® A 50 (protective colloid from BASF Aktiengesellschaft) in 17 g of Solvesso® 150 was initially taken in the reactor and heated to 90° C. A solution of 5.0 g of tert-butyl peroctoate in 20 g of Solvesso® 150 was added in the course of 3.5 hours. At the same time, 3.85 g of styrene, dissolved in 10 g of solvesso® 150, were metered in over 2.5 hours. After the end of the feed, polymerization was continued for a further 2 hours at 100° C. The yellowish brown suspension thus obtained had a solids content of 70.4% and was reacted directly without further working up.

A11)

A solution of 130.3 g of a diester of fumaric acid, prepared by esterification with a $C_{12/14}$-alkyl alcohol (ALFOL® 1412 H from Condea), in 37 g of o-xylene was initially taken in the reactor and heated to 90° C. The following feeds were then metered in simultaneously in the stated times: 29.6 g of $C_{20/24}$-olefin (Gulftene® 20–24), dissolved in 21 g of Solvesso® 150 (3 h), 33.6 g of diketene, dissolved in 134 g of Solvesso® 150 (3 h) and 9.7 g of tert-butyl peroctoate, dissolved in 40 g of Solvesso® 150 (3.5 h). After the end of the feed, polymerization was continued for a further 2 hours at 100° C. The yellow oily polymer solution thus obtained had a solids content of 41.2% and was reacted directly without further working up.

B) Reaction of the novel polymers A) with ethoxylated fatty alcohols

General method:

The corresponding amount of the ethoxylated stearyl alcohol (Lutensol® AT brands from BASF Aktiengesellschaft) or of the alkyl alcohol was added to the amount of polymer solution A) stated in Table 1 and the mixture was diluted with the stated amount of Solvesso® 150 and then heated at 100° C. for 5 hours. The end of the reaction could be detected by IR spectroscopy. The carbonyl vibration of the lactone having a 4-membered ring and of the carboxylic anhydride group at 1840 $cm^{-1}$ decreased while an ester band appeared at 1730 $cm^{-1}$.

TABLE 1

| Example | Polymer | Alcohol component | Solvesso ® 150 |
| --- | --- | --- | --- |
| B1 | 18.5 g A3 | 57.6 g Lutensol AT 25 | 30 g |
| B2 | 11.6 g A3 | 61.4 g Lutensol AT 50 | 55 g |
| B3 | 13.5 g A5 | 43.0 g Lutensol AT 25 | 40 g |
| B4 | 9.0 g A5 | 49.0 g Lutensol AT 50 | 45 g |
| B5 | 6.7 g A2 | 49.0 g Lutensol AT 50 | 48 g |

TABLE 1-continued

| Example | Polymer | Alcohol component | Solvesso ® 150 |
| --- | --- | --- | --- |
| B6 | 7.9 g A6 | 7.7 g Lutensol AT 11 | 9 g |
| B7 | 7.9 g A6 | 14.4 g Lutensol AT 25 | 16 g |
| B8 | 12.2 g A3 | 13 g 2-ethylhexanol | 35 g |
| B9 | 36.6 g A6 | 21,5 g oleyl alkohol | 25 g |

C) Reaction of the novel polymers A) with amines

General method:

The corresponding amount of the amine component was added to the amount of a polymer solution A) stated in Table 2 and the mixture was diluted with the stated amount of Solvesso® 150 and then heated at 100° C. for 8 hours. The end of the reaction could be detected by IR spectroscopy. The carbonyl vibration of the lactone having a 4-membered ring or of the carboxylic anhydride group at 1840 $cm^{-1}$ decreased while an amide band appeared at 1650 or 1680 $cm^{-1}$. A decrease in the acid number was observed at the same time.

TABLE 2

| Example | g | Polymer | g | Amine component | g Solvesso ® 150 |
| --- | --- | --- | --- | --- | --- |
| C1 | 20.7 | A1 | 42.0 | distearylamine | 62 g |
| C2 | 25.5 | A3 | 22.2 | distearylamine | — |
| C3 | 32.9 | A4 | 5.1 | distearylamine | — |
| C4 | 28.0 | A5 | 25.3 | distearylamine | — |
| C5 | 33.8 | A7 | 25.3 | distearylamine | — |
| C6 | 30.9 | A8 | 25.3 | distearylamine | — |
| C7 | 6.1 | A1 | 16.3 | N-tallow fat-1,3-diamino propane | 75 g |
| C8 | 9.4 | A2 | 16.3 | N-tallow fat-1,3-diamino-propane | 70 g |
| C9 | 12.2 | A3 | 12.9 | 2-ethylhexyl-amine | 35 |
| C10 | 11.2 | A5 | 16.1 | oleylamine | 35 |
| C11 | 23.9 | A6 | 16.26 | N-tallow fat-1,3-diamino-propane | 15 |
| C12 | 4.8 | A7 | 24.7 | distearylamine | 25 |
| C13 | 5.0 | A8 | 24.7 | distearylamine | 25 |

D. Examples of use

The novel copolymers were tested in a number of mineral oil middle distillates. These were diesel fuels of commercial German refinery quality; they are referred to as DK 1, DK 2 and DK 3:

|  | DK 1 | DK 2 | DK 3 |
| --- | --- | --- | --- |
| Cloud point CP (°C.) | −8 | −7 | −5 |
| CFPP (°C.) | −10 | −9 | −8 |
| Density at 20° C. (g/ml) | 0.831 | 0.826 | 0.838 |
| Initial boiling point (°C.) | 175 | 172 | 167 |
| 20% boiling point (°C.) | 223 | 217 | 221 |
| 90% boiling point (°C.) | 314 | 321 | 328 |
| Final boiling point (°C.) | 352 | 356 | 361 |

2.1 Description of the test methods

The amounts, stated in the tables, of the novel copolymers B1 to B7 and C1 to C6 and/or a known flow improver F1 based on an ethylene/vinyl propionate copolymer containing about 40% by weight of vinyl propionate and having an average molecular weight of 2500 were added to the middle distillates at 40° C. while stirring, and the mixtures were then cooled to room temperature.

Test 1

The additive-containing middle distillates were stored in 100 ml measuring cylinders for 20 hours in a refrigerator at −13° C. Thereafter, the volume and appearance of both the paraffin phase which had settled out and the supernatant oil phase were visually determined and evaluated. In addition, the cold filter plugging point (CFPP) according to DIN EN 116 was measured for every sample.

The results are shown in Table 3. It is evident that very good dispersing of the n-paraffins is achieved by the novel copolymers B1 to B7 in the presence of the flow improver F1. In contrast, the flow improver F1 alone has no dispersing effect.

TABLE 3

Dispersing experiments (Test 1) in DK 1, CP: −8° C., CFPP: −10° C.

| Example | Dose (ppm) | F1 dose (ppm) | CFPP (°C.) | Paraffin phase (% by vol.) | Appearance | Oil phase (% by vol.) | Appearance |
|---|---|---|---|---|---|---|---|
| B1 | 300 | 300 | −28 | 100 | dispersed | 0 | — |
| B2 | 300 | 300 | −25 | 100 | dispersed | 0 | — |
| B3 | 300 | 300 | −26 | 100 | dispersed | 0 | — |
| B4 | 300 | 300 | −27 | 100 | dispersed | 0 | — |
| B5 | 300 | 300 | −27 | 85 | dispersed | 15 | clear |
| B6 | 300 | 300 | −29 | 100 | dispersed | 0 | — |
| B7 | 300 | 300 | −29 | 100 | dispersed | 0 | — |
| — | — | 300 | −27 | 30 | settled out | 70 | clear |

Test 2

The additive-containing middle distillates were cooled from room temperature to −13° C. in 500 ml glass cylinders in a cold bath and stored at this temperature for 20 hours. Thereafter, the amount and appearance of the paraffin phase were visually determined and evaluated. The cold filter plugging point (CFPP) according to DIN EN 116 and the cloud point (CP) according to ASTM D 2500 were determined for each sample of the 20% by volume lower phase separated off at −13° C.

The results are shown in Tables 4 to 6. In addition to the visual evaluation, the good agreement of the CP of the 20% by volume lower phase with the CP of the particular middle distillate shows that virtually complete dispersing of the n-paraffins was achieved.

TABLE 4

Dispersing experiments (Test 2) in DK 1, CP: −8° C., CFPP: −10° C.

| Example | Dose (ppm) | F1 Dose (ppm) | CFPP (°C.) | Paraffin phase (% by volume) | Appearance | 20% Lower phase CFPP (°C.) | CP (°C.) |
|---|---|---|---|---|---|---|---|
| C1 | 300 | 300 | −21 | 100 | dispersed | −21 | −9 |
| C2 | 300 | 300 | −20 | 0 | — | −20 | −9 |
| C3 | 300 | 300 | −19 | 100 | dispersed | −19 | −9 |
| C4 | 300 | 300 | −30 | 100 | dispersed | −28 | −8 |
| C5 | 300 | 300 | −28 | 100 | dispersed | −28 | −9 |
| C6 | 300 | 300 | −20 | 100 | dispersed | −20 | −9 |
| C8 | 300 | 300 | −23 | 100 | dispersed | −23 | −9 |
| C12 | 300 | 300 | −28 | 100 | dispersed | −28 | −9 |
| C13 | 300 | 300 | −20 | 100 | dispersed | −20 | −9 |

TABLE 5

Dispersing experiments (Test 2) in DK 2, CP: −7° C., CFPP: −9° C.

| | | | | Paraffin phase | | 20% Lower phase | |
|---|---|---|---|---|---|---|---|
| Example | Dose (ppm) | F1 Dose (ppm) | CFPP (°C.) | (% by volume) | Appearance | CFPP (°C.) | CP (°C.) |
| C1 | 300 | 300 | −28 | 100 | dispersed | −29 | −6 |
| C2 | 300 | 300 | −17 | 100 | dispersed | −12 | −5 |
| C3 | 300 | 300 | −16 | 90 | dispersed | −16 | −7 |
| C4 | 300 | 300 | −28 | 100 | dispersed | −20 | −5 |

TABLE 6

Dispersing experiments (Test 2) in DK 3, CP: −5° C., CFPP: −8° C.

| | | | | Paraffin phase | | 20% Lower phase | |
|---|---|---|---|---|---|---|---|
| Example | Dose (ppm) | F1 Dose (ppm) | CFPP (°C.) | (% by volume) | Appearance | CFPP (°C.) | CP (°C.) |
| C4 | 300 | 300 | −28 | 100 | dispersed | −20 | −1 |
| C5 | 300 | 300 | −21 | 100 | dispersed | −21 | −3 |
| C6 | 300 | 300 | −20 | 100 | dispersed | −20 | −3 |
| C8 | 300 | 300 | −19 | 100 | dispersed | −19 | −5 |
| B8 | 300 | 300 | −23 | 90 | dispersed | −20 | −5 |

We claim:

1. A copolymer comprised of a) from 1 to 65 mol % of at least one diketene of formula I

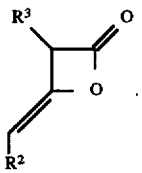

where $R^1$ and $R^2$, independently of one another, are each hydrogen or $C_1$–$C_{30}$-alkyl, b) from 30 to 70 mol % of at least one ethylenically unsaturated dicarboxylic acid or one dicarboxylic acid derivative, c) from 0.5 to 60 mol % of at least one ethylenically unsaturated hydrocarbon and d) up to 20 mol % of at least one further ethylenically unsaturated monomer, wherein said ethylenically unsaturated hydrocarbon is selected from the group consisting of α-olefin and poly(α-olefin)derivatives having a terminal C-C double bond.

2. A copolymer as claimed in claim 1, wherein $R^1$ and $R^2$ are each hydrogen.

3. A copolymer as claimed in claim 1, wherein the ethylenically unsaturated dicarboxylic acid or dicarboxylic acid derivative b) is of the formula IIa or IIb

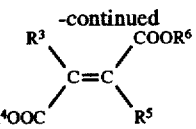

where $R^3$ to $R^6$, independently of one another, are each hydrogen or a $C_1$–$C_{22}$-alkyl radical which may contain hetero atoms, or are the anhydride of the particular cis-dicarboxylic acid of the formula IIa.

4. A copolymer as claimed in claim 3, wherein $R^3$ and $R^5$ are each hydrogen.

5. A copolymer as claimed in claim 1, wherein the ethylenically unsaturated hydrocarbons are of the formula III

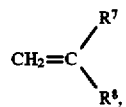

where $R^7$ is hydrogen or $C_1$–$C_{10}$-alkyl and $R^8$ is alkyl, alkenyl or aryl.

6. A modified copolymer which is suitable as paraffin dispersant and is obtained by reacting a copolymer of a) from 1 to 65 mol % of at least one diketene of formula I

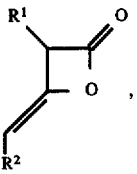

where $R^1$ and $R^2$, independently of one another, are each hydrogen or $C_1$–$C_{30}$-alkyl, b) from 30 to 70 mol % of at least one ethylenically Unsaturated dicarboxylic acid or one dicarboxylic acid derivative, c) from 0.5 to 60 mol % of at least one ethylenically unsaturated hydrocarbon and d) up to 20 mol % of at least one further ethylenically unsaturated monomer, with NH-, SH- or OH-functional compounds.

7. A modified copolymer as claimed in claim 6, wherein the NH- or OH-functional compound used is a compound of the formula IV

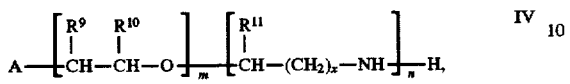

where m may be from 0 to 100, n from 0 to 5 and x from 0 to 5, $R^9$, $R^{10}$ and $R^{11}$, independently of one another, are each hydrogen or $C_1$–$C_5$-alkyl, and A is $NR^{12}R^{13}$ or $C_2$–$C_{30}$-alkoxy, and at least one of the substituents $R^{12}$ or $R^{13}$ is not hydrogen and is $C_1$–$C_{30}$-alkyl or alkenyl or a polyether radical

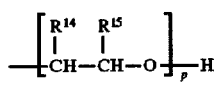

where $R^{14}$ and $R^{15}$ are each hydrogen or $C_1$–$C_5$-alkyl and p is from 1 to 100.

8. A mineral oil middle distillate containing a copolymer as claimed in claim 1.

9. A process for the preparation of a copolymer as claimed in claim 1, wherein a) from 1 to 65 mol % of at least one diketene of formula I

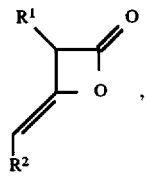

where $R^1$ and $R^2$, independently of one another, are each hydrogen or $C_1$–$C_{30}$-alkyl, b) from 30 to 70 mol % of at least one ethylenically unsaturated dicarboxylic acid or one dicarboxylic acid derivative, c) from 0.5 to 60 mol % of at least one ethylenically unsaturated hydrocarbon and d) up to 20 mol % of at least one further ethylenically unsaturated monomer, are reacted in the presence of a free radical polymerization initiator.

* * * * *